United States Patent
Bernhard et al.

(10) Patent No.: US 11,873,285 B2
(45) Date of Patent: Jan. 16, 2024

(54) PROCESS FOR MAKING PROPENE OXIDE

(71) Applicants: Evonik Operations GmbH, Essen (DE); thyssenkrupp Uhde GmbH, Dortmund (DE)

(72) Inventors: Maik Bernhard, Radeburg (DE); Juliette Halli, Frankfurt am Main (DE); Marc Brendel, Bruchkoebel (DE); Sören Götz, Kahl am Main (DE); Hans-Christian Dietz, Hattersheim (DE)

(73) Assignees: Evonik Operations GmbH, Essen (DE); thyssenkrupp Uhde GmbH, Dortmund (DE)

( * ) Notice: Subject to any disclaimer, the term of this patent is extended or adjusted under 35 U.S.C. 154(b) by 0 days.

(21) Appl. No.: 18/046,150

(22) Filed: Oct. 12, 2022

(65) Prior Publication Data

US 2023/0120363 A1    Apr. 20, 2023

(30) Foreign Application Priority Data

Oct. 14, 2021 (EP) .................................... 21202651

(51) Int. Cl.
*C07D 301/12* (2006.01)
*C07D 301/32* (2006.01)
*C07D 303/04* (2006.01)

(52) U.S. Cl.
CPC ......... *C07D 301/12* (2013.01); *C07D 301/32* (2013.01); *C07D 303/04* (2013.01)

(58) Field of Classification Search
CPC .. C07D 301/12; C07D 301/32; C07D 303/04; Y02P 20/52
USPC ........................................................ 549/531
See application file for complete search history.

(56) References Cited

U.S. PATENT DOCUMENTS

2004/0110970 A1    6/2004 Haas et al.

FOREIGN PATENT DOCUMENTS

WO    2018/205244    11/2018

OTHER PUBLICATIONS

Wikipedia, Sulfuric acid , Sep. 2019 , p. 1-20 (Year: 2019).*
Extended European Search Report dated Mar. 25, 2022, in European Application No. 21202651.2, 8 pages.
U.S. Appl. No. 17/787,254, filed Dec. 16, 2020, Lizio et al.
U.S. Appl. No. 17/785,236, filed Dec. 16, 2020, Lizio et al.
U.S. Appl. No. 18/263,796, filed Aug. 1, 2023, Bernhard et al.
Benje et al., U.S. Appl. No. 18/559,734, filed Nov. 8, 2023.
U.S. Appl. No. 18/559,734, filed Nov. 8, 2023, Benje et al.

* cited by examiner

*Primary Examiner* — Taylor V Oh
(74) *Attorney, Agent, or Firm* — Grüneberg and Myers PLLC

(57) ABSTRACT

A process for making propene oxide involves reacting propene with hydrogen peroxide in the presence of methanol, a titanium zeolite epoxidation catalyst, and nitrogen containing compounds present in an amount of from 100 to 3000 mg/kg of hydrogen peroxide. Non-reacted propene is separated from the reaction mixture; the propene depleted reaction mixture is continuously distilled in a distillation column providing an overhead product stream containing propene oxide and methanol and a bottoms product stream; and propene oxide is separated from the overhead product stream. An acid is added to the propane depleted reaction mixture and/or to the distillation column at the same level or above the feed point for the propene depleted reaction mixture and/or contacted to the feed to the distillation column to provide an apparent pH in the bottoms product stream of from 3 to 4.5, which reduces the nitrogen content of the separated propene oxide.

16 Claims, No Drawings

PROCESS FOR MAKING PROPENE OXIDE

CROSS-REFERENCE TO RELATED APPLICATIONS

This application claims priority to European Application No. 21202651.2, fled on Oct. 14, 2021, the content of which is hereby incorporated by reference in its entirety.

BACKGROUND OF THE INVENTION

Field of the Invention

The invention is directed at a process for making propene oxide from propene and hydrogen peroxide which propene oxide has a low content of nitrogen compounds.

Description of Related Art

The epoxidation of propene with hydrogen peroxide in the presence of a titanium silicalite catalyst is known from EP 0 100 119 A1. The reaction of propene with hydrogen peroxide in the presence of a titanium zeolite catalyst is usually carried out in a methanol solvent to achieve high reaction rates and product selectivity. In addition to propene oxide, the epoxidation reaction produces byproducts from reaction or propene oxide with water or methanol, such as 1,2-propanediol, 1-methoxy-2-propanol and 2-methoxy-1-propanol, and from oxidative glycol cleavage, such as formaldehyde, acetaldehyde.

EP 0 230 949 A1 describes that neutralization of the titanium silicalite catalyst improves selectivity for propene oxide by reducing the formation of byproducts 1,2-propanediol, 1-methoxy-2-propanol and 2-methoxy-1-propanol. Ammonia can be used for neutralizing the catalyst.

WO 01/57010 and WO 03/018567 describe a work-up of the reaction mixture of epoxidizing propene with hydrogen peroxide in a methanol solvent, where the depressurized reaction mixture is separated in a pre-evaporator to provide an overhead product comprising propene oxide and from 20 to 60% of the introduced methanol and a bottoms product containing water and the remainder of the methanol in order to minimize propene oxide hydrolysis in the work-up of the reaction mixture.

WO 2004/048355 discloses a method for removing both methanol and acetaldehyde from a crude propene oxide in a single distillation column by an extractive distillation where a compound containing an unsubstituted $NH_2$ group and capable of reacting with acetaldehyde at the conditions of distillation is additionally fed at or above the feeding point of the crude propene oxide. An aqueous hydrazine solution is preferably used as the additionally fed compound. Water is particularly preferred as the extraction solvent. The method provides propene oxide of high purity for making polyether polyols.

SUMMARY OF THE INVENTION

The Inventors of the present invention have observed that propene oxide, made by epoxidation of propene with hydrogen peroxide where ammonia is added for neutralizing the titanium zeolite epoxidation catalyst, may contain nitrogen compounds in amounts which can lead to quality problems if the propene oxide is further processed to a polyether polyol and a polyurethane derived from the polyether polyol. The inventors have found that a propene oxide having a reduced content of nitrogen compounds can be provided by working up the reaction mixture of the epoxidation reaction by removal of propene, followed by a continuous distillation separating the propene depleted reaction mixture into an overhead product stream comprising propene oxide and methanol and a bottoms product stream comprising methanol and water where an acid is added to the continuous distillation in an amount adjusting the apparent pH of the bottoms product within a specific pH range where entrainment of nitrogen containing compounds in the overhead product stream can be reduced and product losses by hydrolysis and solvolysis of propene oxide can be kept low.

Subject of the invention is therefore a process for making propene oxide comprising the steps a) reacting propene with hydrogen peroxide in the presence of a methanol solvent, of a titanium zeolite epoxidation catalyst and of at least one nitrogen containing compound present in an amount of from 100 to 3000 mg/kg of hydrogen peroxide, at a molar excess of propene to hydrogen peroxide to provide a reaction mixture;

b) separating all or a part of non-reacted propane from the reaction mixture of step a) to provide a propene depleted reaction mixture;

c) subjecting the propene depleted reaction mixture of step b) to a distillation in a distillation column providing an overhead product stream comprising propane oxide and methanol and a bottoms product stream comprising methanol and water;

d) and separating propene oxide from the overhead product stream of step c);

wherein step c) is performed after contact with and/or in presence of an acid provided in an amount providing an apparent pH in the bottoms product stream of from 3 to 4.5.

The invention also includes the following embodiments:

1. A process for making propene oxide comprising the steps a) reacting propene with hydrogen peroxide in the presence of a methanol solvent, of a titanium zeolite epoxidation catalyst and of at least one nitrogen containing compound present in an amount of from 100 to 3000 mg/kg of hydrogen peroxide, at a molar excess of propene to hydrogen peroxide to provide a reaction mixture;

b) separating all or a part of non-reacted propene from the reaction mixture or step a) to provide a propane depleted reaction mixture;

c) subjecting the propene depleted reaction mixture of step b) to a distillation in a distillation column providing an overhead product stream comprising propene oxide and methanol and a bottoms product stream comprising methanol and water;

d) and separating propene oxide from the overhead product stream of step c);

characterized in that step c) is performed after contact with and/or in presence of an acid provided in an amount providing an apparent pH in the bottoms product stream of from 3 to 4.5.

2. The process of embodiment 1, wherein said nitrogen containing compound is ammonia and the molar ratio of the acid provided in step c) to the ammonia contained in the propene depleted reaction mixture of step b) is from 0.025 to 2.

3. The process of embodiment 1 or 2, wherein the acid is added to the propene depleted reaction mixture prior to feeding it to the distillation column.

4. The process of embodiment 1 or 2, wherein the acid is added to the distillation column at a feed point at the same level or above the feed point for the propene depleted reaction mixture.
5. The process of embodiment 1 or 2, wherein the acid is contacted to the propene depleted reaction mixture prior to feeding it to the distillation column.
6. The process of embodiment 5, wherein the acid is supported on a solid carrier.
7. The process of embodiment 1 or 2 wherein a combination of at least two measures as defined in embodiments 3, 4, 5 or 6 are performed.
8. The process of any one of embodiments 1 to 7, wherein the acid added in step c) has a $pK_a$ of less than 5 in aqueous solution.
9. The process of embodiment 8, wherein the acid is sulfuric acid.
10. The process of any one of embodiments 1 to 9, wherein the distillation column in step c) has less than three theoretical separation stages in a rectifying section
11. The process of embodiment 10, wherein the distillation column in step c) is operated without reflux.

DETAILED DESCRIPTION OF THE INVENTION

In step a) of the process of the invention, propene is reacted with hydrogen peroxide to provide a reaction mixture. The reaction is carried out at a molar excess of propene to hydrogen peroxide and in in the presence of a methanol solvent, of a titanium zeolite epoxidation catalyst and of at least one nitrogen containing compound present in an amount of from 100 to 3000 mg/kg of hydrogen peroxide. A prominent example for such nitrogen containing compound is ammonia.

Propene is used in a molar excess to hydrogen peroxide, preferably at a molar ratio of propene to hydrogen peroxide of from 1.1:1 to 30:1, more preferably 2:1 to 10:1 and most preferably 3:1 to 5:1. In a preferred embodiment, propene is used in an excess sufficient to maintain an additional liquid phase rich in propene throughout step a). The propene may contain propane, preferably with a molar ratio of propane to propene of from 0.001 to 0.20 and more preferably of from 0.08 to 0.12.

Hydrogen peroxide can be used as an aqueous solution, preferably containing from 30 to 75% by weight hydrogen peroxide and most preferably from 40 to 70% by weight. The aqueous hydrogen peroxide solution is preferably made by an anthraquinone process.

The reaction of propene with hydrogen peroxide is carried out in the presence of a methanol solvent. The methanol solvent can be a technical grade methanol, a solvent stream recovered in the work-up of the epoxidation reaction mixture or a mixture of both. The methanol solvent may comprise other solvents in minor amounts, such as ethanol, with the amount of such other solvents preferably being less than 2% by weight. The methanol solvent may also comprise water, preferably from 2 to 13% by weight water. The methanol solvent is preferably used in the epoxidation in a weight ratio of 0.5 to 20 relative to the combined weight of water and hydrogen peroxide.

A titanium zeolite epoxidation catalyst is used in step a) which preferably comprises titanium atoms on silicon lattice positions. Preferably, a titanium silicalite catalyst is used, preferably with an MFI or MEL crystal structure. Most preferably a titanium silicalite-1 catalyst with MFI structure as known from EP 0 100 119 A1, is used. The titanium silicalite catalyst is preferably employed as a shaped catalyst in the form of granules, extrudates or shaped bodies. For the shaping process the catalyst may contain 1 to 99% of a binder or carrier material, all binders and carrier materials being suitable that do not react with hydrogen peroxide or with propene oxide under the reaction conditions employed for the epoxidation, silica being preferred as binder. Extrudates with a diameter of 1 to 5 mm are preferably used as shaped catalysts. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions.

The epoxidation reaction of step a) Is preferably carried out at a temperature of 20 to 80° C., more preferably at 25 to 60° C. The epoxidation reaction is preferably carried out at a pressure that is higher than the vapor pressure of propene at the reaction temperature in order to maintain the propene dissolved in the solvent or present as a separate liquid phase. The pressure in step a) is preferably from 1.9 to 5.0 MPa, more preferably 2.1 to 3.6 MPa and most preferably 2.4 to 2.8 MPa. Using an excess of propene at a high pressure provides high reaction rate and hydrogen peroxide conversion and at the same time high selectivity for propene oxide.

The epoxidation reaction is carried out in the presence of ammonia to improve epoxide selectivity as described in EP 0 230 949 A2. Ammonia is used in an amount of from 100 to 3000 mg/kg of hydrogen peroxide. The ammonia is preferably added to a feed stream to step a).

The epoxidation reaction of step a) Is preferably carried out continuously, more preferably in a fixed bed reactor by passing a mixture comprising propene, hydrogen peroxide and solvent over a fixed bed comprising a shaped titanium zeolite catalyst. The fixed bed reactor is preferably a tube bundle reactor and the catalyst fixed bed is arranged inside the reactor tubes. The fixed bed reactor is preferably equipped with cooling means and cooled with a liquid cooling medium. The temperature profile along the length of the catalyst fixed bed is preferably adjusted to keep the reaction temperature along 70 to 98%, preferably along 80 to 95%, of the length of the catalyst fixed bed within a range of less than 5° C., preferably within a range of from 0.5 to 3° C. The temperature of the cooling medium fed to the cooling means is preferably adjusted to a value 3 to 13° C. lower than the maximum temperature in the catalyst fixed bed. The epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally, it is preferred to pass the reaction mixture through the catalyst bed with a liquid hourly space velocity (LHSV) from 1 to 20 $h^{-1}$, preferably 1.3 to 15 $h^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. The epoxidation reaction is most preferably carried out with a catalyst fixed bed maintained in a trickle bed state at a pressure close to the vapor pressure of propene at the reaction temperature, using an excess of propene that provides a reaction mixture comprising two liquid phases, a solvent rich phase and a propene rich liquid phase. Two or more fixed bed reactors may be operated in parallel or in series in order to be able to operate the epoxidation process continuously when regenerating the epoxidation catalyst.

In step b) of the process of the Invention, all or a part of the non-reacted propene is separated from the reaction mixture of step a) to provide a propene depleted reaction mixture. Non-reacted propene may be separated from the reaction mixture of step a) by any method known from the prior art. Preferably, non-reacted propene is separated from the reaction mixture of step a) by a pressure reduction. Propene vapor formed by the pressure reduction is preferably recompressed and cooled to recover propene by condensation. The pressure reduction is preferably carried out in at least two stages with corresponding stages of recompression as described in WO 2017/089079. The compressed propene vapor is preferably fed to a propene distillation column and separated into an overhead product comprising non-reacted propene and a bottoms product containing compounds having a boiling point higher than propene, such as propene oxide and methanol solvent. The overhead product comprising non-reacted propene can be recycled to the epoxidation reaction. The bottoms product can be combined with the propene depleted reaction mixture remaining after the pressure reduction.

In step c) of the process of the Invention, the propene depleted reaction mixture of step b) is subjected to a distillation in a distillation column which provides an overhead product stream comprising propene oxide and methanol and a bottoms product stream comprising methanol and water. In industrial context, such is distillation is usually performed continuously. The distillation column preferably has from 5 to 20 theoretical separation stages in the stripping section and preferably has less than 3 theoretical separation stages in a rectifying section. The distillation column is preferably operated without reflux and preferably without a rectifying section to minimize the residence time of propene oxide in the distillation column. The distillation column is preferably operated at a pressure of from 0.16 to 0.3 MPa. The distillation column is preferably operated to provide an overhead product comprising from 20 to 60% of the methanol contained in the propene depleted reaction mixture of step b).

According to the invention, the distillation is performed in presence of an acid and/or alter contact with an acid, wherein the acid is provided in an amount providing an apparent pH in the bottoms product stream of from 3 to 4.5. Adding and/or contacting the acid in an amount which provides an apparent pH in the bottoms product stream of from 3 to 4.5 reduces carry-over of nitrogen containing compounds from the propene depleted reaction mixture into the overhead product stream comprising propene oxide and methanol with no significant loss of propene oxide by acid catalyzed hydrolysis and solvolysis in the distillation column which would occur at lower apparent pH in the bottoms product stream.

From a technical point of view, there are several solutions to perform inventive acid treatment: The easiest way is using a liquid acid that can be admixed to the propene depleted reaction mixture obtained in step b) before feeding it to the distillation column. Alternatively, the liquid acid can be fed separately to the distillation column at a feed point at the same level or above the feed point for the propene depleted reaction mixture. Yet another option is contacting the acid to the propene depleted reaction mixture obtained in step b) before feeding it to the distillation column. In this context, "contact" means acid treatment without mixing. This can be achieved by using a solid acid. The solid acid can be provided in a bed through which the propene depleted reaction mixture is driven before entering the distillation column. Solid acids are technically realized by loading a liquid acid on a solid carrier. Such solid acid systems are known as ion exchange resins.

While voting for only one technical option for adjusting bottoms pH is preferred, it is also possible to combine several measures. In such case, the acid dosing in each measure needs to be adjusted that the desired pH of the bottoms product stream of the distillation column is achieved.

The desired pH relates to the apparent pH. The term "apparent pH" here refers to a value determined by measurement with a glass electrode employing a commercial pH meter calibrated with aqueous buffer solutions of known pH for measuring dilute aqueous solutions. This apparent pH differs from the notional pH, i.e. the negative logarithm of the hydrogen ion activity, by a constant value because the normal potential of the glass electrode in the bottoms product stream, which comprises methanol and non-reacted hydrogen peroxide, is different than the normal potential in pure water. Desired value of apparent pH is within the range from 3 to 4.5. Preferably, the apparent pH amounts to a value between 3.5 and 4.5.

Preferably, in step c) the acid is added either to the propene depleted reaction mixture prior to feeding it to the distillation column or is added to the distillation column at a feed point at the same level or above the feed point for the propene depleted reaction mixture. The acid is added in an amount providing an apparent pH in the bottoms product stream of from 3 to 4.5 and preferably of from 3.5 to 4.5. The amount of acid added depends from the nitrogen containing compound present in the propene deleted reaction mixture. In case the nitrogen containing compound is ammonia, the molar ratio of the provided acid to the ammonia contained in the propene depleted reaction mixture of step b) is from 0.025 to 2, preferably from 0.025 to 0.3. The acid may be an organic acid, such as a carboxylic acid or a sulfonic acid, or an inorganic acid. The acid preferably has a pKa of less than 5 in aqueous solution, more preferably in the range of from −10 to 4.9. Preferably sulfuric acid is added in step c).

In step d) of the process of the invention, propene oxide is separated from the overhead product stream of step c), preferably by one or more distillations which are preferably carried out continuously.

Step d) preferably comprises an extractive distillation in an extractive distillation column. The extractive distillation uses an aqueous extraction solvent to provide purified propene oxide as an overhead product and a bottoms product comprising water and methanol. Additionally, a reactive compound containing at least one unsubstituted $NH_2$ group and capable of reacting with a component having a carbonyl group, preferably an aldehyde, more preferably acetaldehyde and/or propionaldehyde and/or formaldehyde, at the conditions of said extractive distillation to form compounds with a boiling point higher than that of propene oxide is added to the extractive distillation either with a feed stream to the extractive distillation column or directly to the extractive distillation column at a feed point above a feed point for a crude propene oxide. Preferably, a crude propene oxide comprising from 15 to 97% by weight propene oxide and from 2 to 84% by weight methanol is fed to the extractive distillation column.

The extractive distillation column may be a tray column containing discrete trays such as sieve trays or bubble cap trays. The extractive distillation column may also be a packed column and both random packings as well as structured packings, such as metal gauze packings may be used.

The extractive distillation column may also combine sections with discrete trays and sections with packings. The extractive distillation column will in general also comprise at least one overhead condenser and at least one column reboiler. The extractive distillation column preferably has at least two feed points, a feed point A for feeding the crude propene oxide in the middle section of the extractive distillation column and a feed point B for feeding aqueous extraction solvent located above feed point A. The feed points define three sections of the extractive distillation column, a stripping section between the column bottoms and feed point A, an extraction section between feed point A and feed point B and a rectifying section between feed point B and the top of the extractive distillation column. Preferably a distillation column is used that has a separation efficiency of 10 to 30 theoretical stages in the stripping section, a separation efficiency of 15 to 40 theoretical stages in the extraction section and a separation efficiency of 20 to 60 theoretical stages in the rectifying section, i.e. feed point B is preferably located from 15 to 40 theoretical separation stages above feed point A and from 20 to 80 theoretical separation stages below the top of the extractive distillation column.

The aqueous extraction solvent preferably comprises more than 80% by weight water, more preferably more than 90% by weight water. Preferably, the aqueous extraction solvent comprises no further solvent in addition to water. The extractive distillation is preferably operated continuously and the extraction solvent is fed to the extractive distillation column at a rate providing a mass ratio of the extraction solvent relative to the amount of methanol contained in the crude propene oxide feed of from 0.01 to 1, more preferably from 0.03 to 0.2. The use of such an amount of aqueous extraction solvent provides effective extraction of methanol and a propene oxide product with a low content of methanol and at the same time avoids hydrolysis of propene oxide in the extractive distillation column.

The reactive compound is preferably fed to the extractive distillation column admixed with the extraction solvent. The amount of the reactive compound fed to the distillation column is preferably chosen so that the molar ratio of the reactive compound relative to the compound having a carbonyl group is in the range of from 0.25 to 10. Preferably, said range extends from 0.5 to 10, more preferably from 3 to 8. The precise amount of the molar ratio depends from the number of actually reacting $NH_2$ groups of reactive compound: A reactive compound having several $NH_2$ group needs to be added in a lower ratio to the carbonyl containing compound than a reactive component having only one $NH_2$ group. However, even if the reactive compound bears several $NH_2$ groups, not in every case every $NH_2$ group is reacting with the carbonyl component. Thus, the number of actually reacting $NH_2$ groups is ruling the molar ration of the reactive compound to the carbonyl containing compound. The use of such an amount of a reactive compound provides effective conversion of carbonyl compounds to high boiling compounds and provides a propene oxide product with a low content of acetaldehyde and other carbonyl compounds. At the same time, by-product formation by reactions of the reactive compound with propene oxide can be kept at a low level. In a preferred embodiment, the reactive compound has a structure $R^1$—Y—$NH_2$, where Y is oxygen or $NR^2$ and $R^1$ and $R^2$ independently of one another are hydrogen, an alkyl group or an aryl group. Salts of these reactive compounds with a protonated $NH_2$ group may be used as well. Preferred compounds of structure $R^1$—Y—$NH_2$ are hydrazine, hydrazine monohydrate, hydrazinium salts, hydroxylamine and hydroxylammonium salts. In an alternative preferred embodiment, the reactive compound is a diaminoalkane having from 2 to 6 carbon atoms, preferably 1,2-diaminoethane, 1,2-diaminopropane or 1,3-diaminopropane and most preferably 1,2-diaminoethane. The amount of reactive compound fed to the distillation column is then preferably chosen so that the molar ratio of the reactive compound relative to acetaldehyde is in the range of from 0.5 to 10, more preferably from 3 to 8. Compared to a reactive compound or structure $R^1$—Y—$NH_2$, the use or a diaminoalkane as reactive compound reduces the Formation of volatile amines when reaction products resulting from the reaction of acetaldehyde with the reactive compound containing an $NH_2$ group are hydrogenated in a subsequent step of hydrogenating the bottoms product of the extractive distillation.

In a preferred embodiment, step d) comprises a step of stripping propene from the overhead product stream of step c) prior to an extractive distillation as described in the preceding paragraphs. Preferably, propene oxide and methanol are condensed from the overhead product stream of step c) and propene is stripped from the resulting condensate in a propene stripping column which provides a bottom stream comprising propene oxide and methanol which is essentially free of propene. The stripped propene is preferably combined with propene vapor formed by a pressure reduction step and is recompressed as described further above.

In a further embodiment of the invention, the overhead product stream of step c), optionally after stripping propene, is mixed with an aqueous alkaline solution and the resulting mixture is reacted for 1 to 200 minutes, preferably for 1 to 60 minutes, at a temperature of from 20 to 100° C. before the mixture is fed to the extractive distillation. The aqueous alkaline solution is preferably an aqueous solution of sodium hydroxide, potassium hydroxide, or sodium carbonate. Most preferred are aqueous sodium hydroxide solutions containing from 0.1 to 58% by weight sodium hydroxide. The amount of the aqueous alkaline solution is preferably chosen so that the molar ratio of hydroxide ions introduced with the aqueous alkaline solution relative to the amount of methyl formate contained in the crude propene oxide is in the range from 1.1 to 4. Reacting the overhead product stream of step c) with an aqueous alkaline solution converts methyl formate contained in the stream by hydrolyzing it to methanol and formate. The purified propene oxide obtained with this embodiment of the invention has a reduced content of methyl formate. Preferably the amount of aqueous alkaline solution is chosen to obtain a purified propene oxide having a content of methyl formate of less than 100 ppm by weight.

The bottoms product stream or step c) which comprises methanol and water is preferably separated in at least one distillation stage to provide a recovered methanol as an overhead product. The bottoms product stream is preferably separated in two subsequent distillation stages providing recovered methanol as an overhead product from both stages. The two distillation stages are preferably operated with a higher pressure in the second stage and overhead product vapor from the second stage is used for heating the bottoms evaporator of the first stage in order to save energy. Preferably, an acid is added to at least one of the distillation stages or prior to the distillation. When the acid is added to a distillation stage, it is preferably added at a feed point above the feed point for the solvent mixture and below the column top. The acid may also be added to the reflux stream of the distillation column. Preferably, the acid is fed prior to the distillation. Adding an acid reduces the content of volatile organic amines in the recovered methanol. The acid is preferably added in an amount providing a content of less than 250 ppm by weight nitrogen in the form of organic nitrogen compounds in the recovered methanol, more preferably in an amount providing a content of less than 50 ppm by weight nitrogen in the form of organic nitrogen compounds. The acid may be a mineral acid, such as nitric acid, sulfuric acid, hydrochloric acid, phosphoric acid or perchloric acid; a sulfonic acid, such as methane sulfonic acid; or a carboxylic acid, such as formic acid, acetic acid, propionic acid, butyric acid, pentanoic acid, hexanoic acid, heptanoic acid, octanoic acid, nonanoic acid, decanoic acid, undecanoic acid, dodecanoic acid, oxalic acid, malonic acid, succinic acid, glutaric acid, adipic acid, maleic acid or fumaric acid. Preferred are sulfuric acid and phosphoric acid, most preferred is sulfuric acid. The amount of nitrogen in the form of organic nitrogen compounds can be determined as the difference between the total amount of nitrogen and the amount of nitrogen in the form of inorganic nitrogen compounds. The total amount of nitrogen can be determined by the Kjeldahl method as described in DIN 53825 or by combustion with oxygen and determination of formed NO by chemiluminescence according to DIN EN 12280. The recovered methanol will usually contain no inorganic compounds other than ammonia and the amount of nitrogen in the form of inorganic nitrogen compounds may therefore be determined by ion chromatography of an acidified sample detecting ammonium ions. The acid is preferably added in an amount providing an apparent pH of from 1.6 to 5.0, more preferably from 1.8 to 4.0, in the bottoms product remaining after recovery of methanol. The recovered methanol is preferably recycled to step a) of the process.

The bottoms product stream of step c) is preferably subjected to a catalytic hydrogenation before it is distilled for recovering methanol. The catalytic hydrogenation is preferably carried out at a hydrogen partial pressure of from 0.5 to 30 MPa, more preferably of from 1 to 25 MPa and most preferably of from 1 to 5 MPa. The temperature is preferably in the range of from 80 to 180° C., more preferably from 90 to 150° C. The catalytic hydrogenation is carried out in the presence of a hydrogenation catalyst, preferably a heterogeneous hydrogenation catalyst. Raney nickel and Raney cobalt may be used as hydrogenation catalyst. Preferably, a supported metal catalyst comprising one or more of metals selected from the group consisting of Ru, Rh, Pd, Pt, Ag, Ir, Fe, Cu, Ni and Co on a catalyst support is used. The metal is preferably platinum, palladium, iridium, ruthenium or nickel and most preferably ruthenium or nickel. The catalyst support can be any solid which is inert and does not deteriorate under the hydrogenation conditions. Suitable as catalyst support are activated carbon, the oxides $SiO_2$, $TiO_2$, $ZrO_2$ and $Al_2O_3$, and mixed oxides comprising at least two of silicon, aluminum, titanium and zirconium. $SiO_2$, $Al_2O_3$ and mixed oxides of silicon and aluminum are preferably used as the catalyst support for the supported metal catalyst. The catalyst support is preferably shaped as spheres, pellets, tablets, granules or extrudates. Preferred are extrudates with a diameter of from 0.5 mm to 5 mm, especially from 1 mm to 3 mm, and a length of from 1 mm to 10 mm. The supported metal catalyst preferably comprises from 0.01 to 60 wt. % metal. Supported noble metal catalysts preferably comprise from 0.1 to 5% metal. Supported nickel and cobalt catalysts preferably comprise from 10 to 60% metal. The supported metal catalyst may be prepared by methods known in the art, preferably by impregnating the catalyst support with a metal salt followed by reducing the metal salt to the catalytically active metal. Suitable supported metal catalysts are commercially available, for example from Clariant under the NISAT® trade name and from Evonik Industries under the Octolyst® trade name. The catalytic hydrogenation converts unreacted hydrogen peroxide to water and the by-product peroxides 1-hydroperoxy-2-propanol and 2-hydroperoxy-1-propanol formed in step a) to 1,2-propanediol and prevents by-product formation by peroxide decomposition in subsequent work-up stages. The catalytic hydrogenation is preferably carried out to a conversion of hydrogen peroxide that provides a hydrogenated solvent mixture containing less than 0.1% by weight hydrogen peroxide. The hydrogenation also converts aldehyde and ketone by-products, such as acetaldehyde, to the corresponding alcohols, with the degree of conversion depending on the catalyst and the reaction conditions used. The conversion of the hydrogenation of acetaldehyde to ethanol can be adjusted by varying the reaction time and the hydrogen partial pressure and the temperature used in the catalytic hydrogenation and is preferably adjusted to provide a hydrogenated solvent mixture comprising from 1 to 1000 mg/kg of acetaldehyde.

If step d) of the process comprises an extractive distillation, the bottoms product of the extractive distillation is preferably combined with the bottoms product stream of step c) prior to recovering methanol. If the bottoms product stream of step c) is subjected to a catalytic hydrogenation, the bottoms product of the extractive distillation is preferably combined with the bottoms product stream of step c) prior to the catalytic hydrogenation. Reaction products resulting from the reaction of aldehydes and ketones with the reactive compound containing an $NH_2$ group will then be hydrogenated, i.e. oximes and hydrazones will be hydrogenated with hydrogenolysis of the oxygen-nitrogen bond or the nitrogen-nitrogen bond and imines win be hydrogenated to the corresponding amines.

EXAMPLES

Example 1 (Comparative)

Propene was epoxidized in a cooled tubular reactor with a catalyst fixed bed of an extruded titanium silicalite catalyst arranged in the reaction tube. A mixture comprising 40% by weight of propene, 7.7% by weight hydrogen peroxide, 3.3% by weight water, 49% by weight of methanol and 40 ppm by weight ammonia was fed to the top of the reactor and passed through the catalyst fixed bed in trickle mode. The pressure in the reactor was kept at 2.7 MPa (abs) by introducing nitrogen. The temperature in the reactor was kept essentially constant at a temperature in the range of from 25 to 60° C., adjusting the temperature during the epoxidation reaction to maintain an essentially constant conversion of hydrogen peroxide of 97.5 to 98%. The reaction mixture exiting the reactor was depressurized to a pressure of 0.25 MPa (abs).

Depressurized reaction mixture was fed at a rate of 8.85 kg/h to the uppermost stage of a pre-separation column having 18 theoretical stages. The pre-separation column was operated continuously without reflux at a pressure of 0.25 MPa (abs) Propene oxide and methanol were condensed from the overhead vapor product of the pre-separation column and propene was stripped from the resulting condensate in a propene stripping column to provide a crude propene oxide as bottoms stream comprising 37% by weight propene oxide and 58% by weight methanol. The bottoms product stream of the pre-separation column had an apparent pH of 4.8 measured with a combination glass electrode model Inlab Routine Pro-ISM from Mettler Toledo.

The crude propene oxide was fed to stage 90 (counted from top) of an extractive distillation column having a separation efficiency of 120 theoretical stages at a rate of 3870 g/h. 130 g/h of a 0.4% by weight aqueous solution of hydrazine hydrate was fed to stage 60 (counted from top) of the extractive distillation column. A purified propene oxide, containing less than 1 mg/kg methanol and less than 1 mg/kg acetaldehyde was obtained as overhead product of the column. The purified propene oxide had a total nitrogen content of 0.6 mg/kg determined by the method of DIN EN 12260 (combustion with oxygen and determination or formed NO by chemiluminescence). The yield of propene oxide was 89.0%, calculated on hydrogen peroxide fed.

Example 2

Example 1 was repeated but a 2% by weight aqueous sulfuric acid was added to the depressurized reaction mixture with a dosing pump at a rate or 20 g/h prior to feeding the depressurized reaction mixture to the pre-separation column.

The bottoms product stream of the pre-separation column had an apparent pH of 3.8. The purified propene oxide contained less than 1 mg/kg methanol and less than 1 mg/kg acetaldehyde and had a total nitrogen content of 0.1 mg/kg. The yield of propene oxide was 88.5%.

Example 3 (Comparative)

Example 1 was repeated with 160 ppm by weight ammonia in the feed mixture to the epoxidation reactor.

The bottoms product stream of the pre-separation column had an apparent pH of 5. The purified propene oxide contained less than 1 mg/kg methanol and 1 mg/kg acetaldehyde and had a total nitrogen content of 0.5 mg/kg. The yield of propene oxide was 86.6%.

Example 4

Example 3 was repeated but a 2% by weight aqueous sulfuric acid was added to the depressurized reaction mixture at a rate of 20 g/h prior to feeding the depressurized reaction mixture to the pre-separation column.

The bottoms product stream of the pre-separation column had an apparent pH of 4. The purified propene oxide contained less than 1 mg/kg methanol and 1 mg/kg acetaldehyde and had a total nitrogen content of 0.3 mg/kg. The yield of propene oxide was 86.7%.

Example 5 (Comparative)

Example 1 was repeated with 80 ppm by weight ammonia in the feed mixture to the epoxidation reactor, adding a 10% by weight aqueous sulfuric acid to the depressurized reaction mixture at a rate of 18 g/h prior to feeding the depressurized reaction mixture to the pre-separation column.

The bottoms product stream of the pre-separation column had an apparent pH of 2.9 and the content of by-products 1-methoxy-2-propanol, 2-methoxy-1-propanol and 1,2-propanediol in the bottoms product stream of the pre-separation column was increased by a factor of about 2 compared to example 1. The purified propene oxide contained 30 mg/kg methanol and 5 mg/kg acetaldehyde and had a total nitrogen content of less than 0.1 mg/kg. The yield of propene oxide was 82.7%.

The invention claimed is:

1. A process for making propene oxide, comprising:
   a) reacting propene with hydrogen peroxide in the presence of a methanol solvent, of a titanium zeolite epoxidation catalyst, and of at least one nitrogen containing compound present in an amount of from 100 to 3,000 mg/kg of hydrogen peroxide, at a molar excess of propene to hydrogen peroxide, to provide a reaction mixture;
   b) separating all or a part of non-reacted propene from the reaction mixture of a), to provide a propene depleted reaction mixture;
   c) subjecting the propene depleted reaction mixture of b) to a distillation in a distillation column, to provide an overhead product stream comprising propene oxide and methanol and a bottoms product stream comprising methanol and water; and
   d) separating the propene oxide from the overhead product stream of c);
   wherein c) is performed after contact with and/or in the presence of an acid provided in an amount providing an apparent pH in the bottoms product stream of from 3 to 4.5.

2. The process of claim 1, wherein said nitrogen containing compound is ammonia, and a molar ratio of the acid provided in c) to the ammonia contained in the propene depleted reaction mixture of b) is from 0.025 to 2.

3. The process of claim 1, wherein the acid is added to the propene depleted reaction mixture prior to feeding the propene depleted reaction mixture to the distillation column.

4. The process of claim 1, wherein the acid is added to the distillation column at a feed point at a same level or above a feed point for the propene depleted reaction mixture.

5. The process of claim 1, wherein the acid is contacted to the propene depleted reaction mixture prior to feeding the propene depleted reaction mixture to the distillation column.

6. The process of claim 5, wherein the acid is supported on a solid carrier.

7. The process of claim 1, wherein a combination of at least two of the following measures are performed:
   an amount of the acid is added to the propene depleted reaction mixture prior to feeding the propene depleted reaction mixture to the distillation column,
   an amount of the acid is added to the distillation column at a feed point at a same level or above a feed point for the propene depleted reaction mixture,
   an amount of the acid is contacted to the propene depleted reaction mixture prior to feeding the propene depleted reaction mixture to the distillation column, and/or
   an amount of the acid is supported on a solid carrier.

8. The process of claim 1, wherein the acid added in c) has a pKa of less than 5 in aqueous solution.

9. The process of claim 8, wherein the acid is sulfuric acid.

10. The process of claim 1, wherein the distillation column in c) has less than three theoretical separation stages in a rectifying section.

11. The process of claim 10, wherein the distillation column in c) is operated without reflux.

12. The process of claim 1, wherein the apparent pH in the bottoms product stream is from 3.5 to 4.5.

13. The process of claim 1, wherein the nitrogen containing compound is ammonia, and a molar ratio of the acid provided in c) to the ammonia contained in the propene depleted reaction mixture of b) is from 0.025 to 0.3.

14. The process of claim 1, wherein the propene oxide separated in d) contains less than 1 mg/kg methanol and less than 1 mg/kg acetaldehyde.

15. The process of claim 1, wherein the propene oxide separated in d) has a total nitrogen content of 0.3 mg/kg or lower.

16. The process of claim 14, wherein the propene oxide separated in d) has a total nitrogen content of 0.3 mg/kg or lower.

* * * * *